United States Patent
Lee et al.

(10) Patent No.: US 6,635,487 B1
(45) Date of Patent: Oct. 21, 2003

(54) FLUORESCENCE STANDARD FOR USE IN MICROFLUIDIC INSTRUMENTS

(75) Inventors: Ernest C. W. Lee, Palo Alto, CA (US); Robert Nagle, Mountain View, CA (US); Richard J. McReynolds, San Jose, CA (US); David Chazan, Palo Alto, CA (US); Robert S. Dubrow, San Carlos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 176 days.

(21) Appl. No.: 09/850,855

(22) Filed: May 7, 2001

Related U.S. Application Data

(60) Provisional application No. 60/204,958, filed on May 17, 2000.

(51) Int. Cl.$^7$ .......................... G01N 31/00; G01N 21/76
(52) U.S. Cl. ................ 436/19; 436/8; 436/164; 436/172; 422/82.05; 422/82.08
(58) Field of Search ................ 436/8, 19, 164, 436/172, 165, 180; 422/82.05, 82.08, 100

(56) References Cited

U.S. PATENT DOCUMENTS

| | | | |
|---|---|---|---|
| 5,689,110 A | * 11/1997 | Dietz et al. | ............... 250/252.1 |
| 5,699,157 A | 12/1997 | Parce | |
| 5,852,495 A | 12/1998 | Parce | |
| 5,976,336 A | 11/1999 | Dubrow et al. | |
| 6,046,056 A | 4/2000 | Parce et al. | |
| 6,100,541 A | * 8/2000 | Nagle et al. | ................. 250/573 |
| 6,233,048 B1 | 5/2001 | Parce | |
| 6,267,858 B1 | 7/2001 | Parce et al. | |
| 6,316,781 B1 | * 11/2001 | Nagle et al. | ................. 250/573 |
| 6,322,683 B1 | * 11/2001 | Wolk et al. | ................. 204/600 |
| 6,475,364 B1 | * 11/2002 | Dubrow et al. | ............. 204/455 |
| 6,495,104 B1 | * 12/2002 | Unno et al. | ................. 422/68.1 |
| 6,498,353 B2 | * 12/2002 | Nagle et al. | ................. 250/573 |
| 6,498,497 B1 | * 12/2002 | Chow et al. | ................. 324/601 |
| 6,506,609 B1 | * 1/2003 | Wada et al. | ................. 436/148 |

FOREIGN PATENT DOCUMENTS

| | | |
|---|---|---|
| WO | WO 98/00231 A1 | 1/1998 |
| WO | WO 98/56956 A1 | 12/1998 |
| WO | WO 01/73417 A1 | 10/2001 |

* cited by examiner

*Primary Examiner*—Maureen M. Wallenhorst
(74) *Attorney, Agent, or Firm*—Andrew L. Filler; Jonathan Alan Quine; Quine Intellectual Property Law Group, P.C.

(57) ABSTRACT

A test device for use as a fluorescent standard in microfluidic analytical detection systems includes one or more slits that correspond to, and are of similar dimension to, one or more microchannels in a detection region on a corresponding analysis chip. A fluorescent material is attached to the test device on the side opposite the illumination source such that excitation radiation passes through the slit(s), which defines the focal plane of the illumination optics, and impinges on the fluorescent material thereby causing the fluorescent material to fluoresce. By displacing the fluorescent material relative to the focal plane, the intensity of the radiation exciting the fluorescent material is dispersed relative to the intensity of the radiation at the focal plane, and concomitantly the strength of the resulting fluorescent signal is reduced. An optional spacer is provided to increase the distance of the fluorescent material from the focal plane so as to increase the dispersion of the radiation (decrease the intensity impinging on the fluorescent material). The strength of the resulting fluorescent signal from the fluorescent material can be controlled by selecting a spacer with the appropriate depth.

20 Claims, 3 Drawing Sheets

FLUORESCENCE STANDARD FOR USE IN MICROFLUIDIC INSTRUMENTS

CROSS REFERENCE TO RELATED APPLICATIONS

This application claims priority to U.S. Provisional Application No. 60/204,958, filed May 17, 2000, the teachings of which are incorporated herein by reference in their entirety for all purposes.

BACKGROUND OF THE INVENTION

The present invention relates to calibration standards for optical illumination and detection systems, and more particularly to fluorescent standards for testing and calibrating microfluidic optical measurement systems.

Optical standards are commonly used to test and calibrate measurement systems. In general, a standard provides a benchmark that is used in a measurement system or device to maintain continuity of value in the units of measurement. In an optical measurement system, for example, an optical standard can be used to provide light having a known wavelength or intensity value to the system.

In a typical fluorescence detection system, a fluorescent material, e.g., a fluorophore, absorbs light having certain wavelengths dependent on the absorption characteristics of the material, and fluoresces (i.e., emits a fluorescent light signal) at a specific wavelength that is greater than the absorbed wavelength. In fluorescence detection systems, a fluorescence standard can be used to provide a fluorescence signal having a known wavelength and/or intensity value. Additionally, a fluorescence standard having a known fluorescent lifetime can be used.

In certain analytical detection systems, known as "microfluidic" systems, fluorescent materials are often used to measure and detect reactions and conditions. In such systems a fluorescent material is transported along a microscale channel to a detection region where the material is excited by an excitation source and the resulting fluorescent signal is measured to determine the presence or absence of some material or condition. Many such microfluidic analytical systems use a substrate or chip having a plurality of buffer and sample reservoirs interconnected by a plurality of microchannels. One or more of the microchannels typically traverse the detection region on the chip. When placed in the appropriate position relative to an illumination source and detector(s) any number of assays involving fluorescent signal detection and measurement can be performed.

To ensure continuity of value in the units of measurement, a test chip having a fluorescent material (i.e., standard) in a location corresponding to the microchannel(s) in the detection region on the assay chips can be appropriately positioned in the system to test and calibrate the illumination and detection components. In such systems, the illumination source and associated optics are designed and configured to focus the excitation radiation onto the microchannel(s) in the detection region of the assay chips. Focussing the radiation at this position provides the greatest intensity to enhance analytical detection measurements on the assay chips. In test chips, the fluorescent material is therefore located at the position corresponding to the location of the detection region. Unfortunately, however, some fluorescent materials may provide too great of a fluorescence signal to be useful when in the presence of such strong, intense excitation radiation. Additionally, some fluorescent materials may photobleach readily in such an environment thereby causing the fluorescence to be non-stable and non-constant. In some cases, photobleaching may damage the standard, requiring the expense of purchasing additional standards. It may be possible to reconfigure the illumination optics to reduce the intensity of radiation applied to the fluorescent material in such test chips, but this too requires additional expense and down time of the analytical system.

Accordingly, what is needed in the art is a fluorescent standard for use in microfluidic optical measurement systems that overcomes the above and other problems.

SUMMARY OF THE INVENTION

The present invention solves the above and other problems by providing a fluorescent standard for use in optical detection systems generally, and optimally for use in microfluidic analytical systems employing fluorescent detection techniques. The present invention provides a fluorescent standard that minimizes photobleaching of the fluorescent material and that supplies a controllably reduced fluorescent signal.

According to the present invention, a test device for use as a fluorescent standard in microfluidic analytical detection systems is provided. The test device is substantially the same size as a corresponding analysis chip for ease of use with the analytical system. The device includes one or more slits that correspond to, and are of similar dimension to, one or more microchannels in a detection region on the corresponding analysis chip. A fluorescent material is attached to a test device on the side opposite the illumination source such that excitation radiation passes through the slit(s), which defines the focal plane of the illumination optics, and impinges on the fluorescent material thereby causing the fluorescent material to fluoresce. By displacing the fluorescent material relative to the focal plane, the intensity of the radiation exciting the fluorescent material is dispersed relative to the intensity of the radiation at the focal plane, and concomitantly the strength of the resulting fluorescent signal is reduced. An optional spacer is provided to increase the distance of the fluorescent material from the focal plane so as to increase the dispersion of the radiation (decrease the intensity impinging on the fluorescent material). Such a device is useful for reducing the effect of photobleaching of the selected fluorescent material and for reducing the strength of the resulting fluorescent signal. Additionally, the strength of the resulting fluorescent signal from the fluorescent material can be controlled by selecting a spacer with the appropriate depth.

According to an aspect of the invention, a device is provided for use in testing microfluidic fluorescence detection systems having a light source and a detector for detecting fluorescent emissions. The device typically comprises a test substrate having a microslit through which light from the light source is able to pass, the microslit defining a first region, and a fluorescent material coupled to the substrate and positioned proximal the microslit, wherein the fluorescent material emits a fluorescent emissions signal when light impinges thereon, wherein when the light is focused onto the first region, at least a portion of the light passes through the microslit and is dispersed relative to the first region when it impinges on the fluorescent material. The device also typically includes a spacer coupling the substrate to the fluorescent material for increasing the amount of dispersion of the light that impinges on the fluorescent material so as to reduce even further the fluorescent signal emitted by the fluorescent material as well as the effect of photobleaching of the fluorescent material.

According to another aspect of the present invention, a device is provided for use in testing microfluidic fluorescence detection systems having a light source and a detector for detecting fluorescent emissions. The device typically comprises a test substrate having a microslit through which light from the light source is able to pass, the microslit defining a first region, and a fluorescent material coupled to the substrate and positioned proximal the microslit and opposite the light source, wherein when the light is focused onto the first region such the light has a first intensity at the first region, at least a portion of the light passes through the microslit and is dispersed such that the light has a second intensity at the fluorescent material, wherein the second intensity is lower than the first intensity, and wherein the fluorescent material emits a fluorescent emissions signal proportional to the intensity of light impinging thereon.

According to a further aspect of the present invention, a method is provided for testing a microfluidic fluorescent detection system having an excitation source and a fluorescence detector. The method typically comprises the steps of providing a test substrate coupled to a fluorescent material, the substrate having a microslit defining a first region through which light from the excitation source is able to pass through to the fluorescent material, and focusing light from the excitation source onto the first region, wherein at least a portion of the light focussed on the first region passes through the microslit so as to excite the fluorescent material. The method also typically includes the step of detecting fluorescent emissions from the excited fluorescent material with the fluorescence detector.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DESCRIPTION OF THE SPECIFIC EMBODIMENTS

In preferred aspects, the methods and apparatus of the present invention are useful for testing and calibrating analytical optical detection systems directed primarily to fluorescence detection in microscale fluidic channels. Examples of such systems include, e.g., fused silica capillary systems, i.e., CE, as well as microfluidic devices and systems that incorporate microscale channels such as microfluidic channels. Such systems are generally described in U.S. Pat. No. 5,976,336 entitled, "Microfluidic Devices Incorporating Improved Channel Geometries" filed Apr. 25, 1997, U.S. Pat. No. 6267.858 issued Jul. 31. 2001 entitled, "High Throughput Screening Assay Systems In Microscale Fluidic Devices" filed Jun. 24,1997 (and corresponding published PCT Application Publication No, 98/00231, published Jan. 8, 1998), which is a continuation-in-part of U.S. Pat. No. 6,046,056 entitled, "High Throughput Screening Assay Systems In Microscale Fluidic Devices," filed Dec. 6, 1996, and U.S. Provisional Patent Application No. 60/049, 013, filed Jun. 9, 1997, The disclosure of each of these applications is hereby incorporated by reference in its entirety for all purposes, it will of course be apparent that the methods and apparatus of the present invention are also useful for testing and calibrating any similar optical detection and measurement systems.

In typical microfluidic analysis systems and devices, a "microfluidic" channel is a channel (enclosed groove, depression, tube, capillary, etc.) which is adapted to handle small volumes of fluid. In a typical embodiment, the channel is a tube, channel or conduit having at least one subsection with at least one cross-sectional dimension of between about 0.1 $\mu$m and 500 $\mu$m, and typically less than 100 $\mu$m; ordinarily, the channel is closed over a significant portion of its length, having top, bottom and side surfaces. In operation, materials that are being analyzed, e.g., subjected to optical analysis for fluorescence emission signals in these microscale fluidic systems are transported along the microscale fluid channels past a detection point where a detectable fluorescence emission signal is measured. The signals within these channels typically result from the presence of fluorescent substances therein, e.g., fluorophores that inherently fluoresce, or are made to fluoresce, that are used as indicators of the presence or absence of some material or condition. Typically, transporting materials within these systems may be carried out by any of a variety of methods. For example, such material transport is optionally carried out through the application of pressures (positive and/or negative pressure) to the materials within the channels, from external sources or through the incorporation of microscale mechanical pumps, or through the application of electric fields (e.g., electrokinetic material transport), to move materials through the channels.

Figure 1:
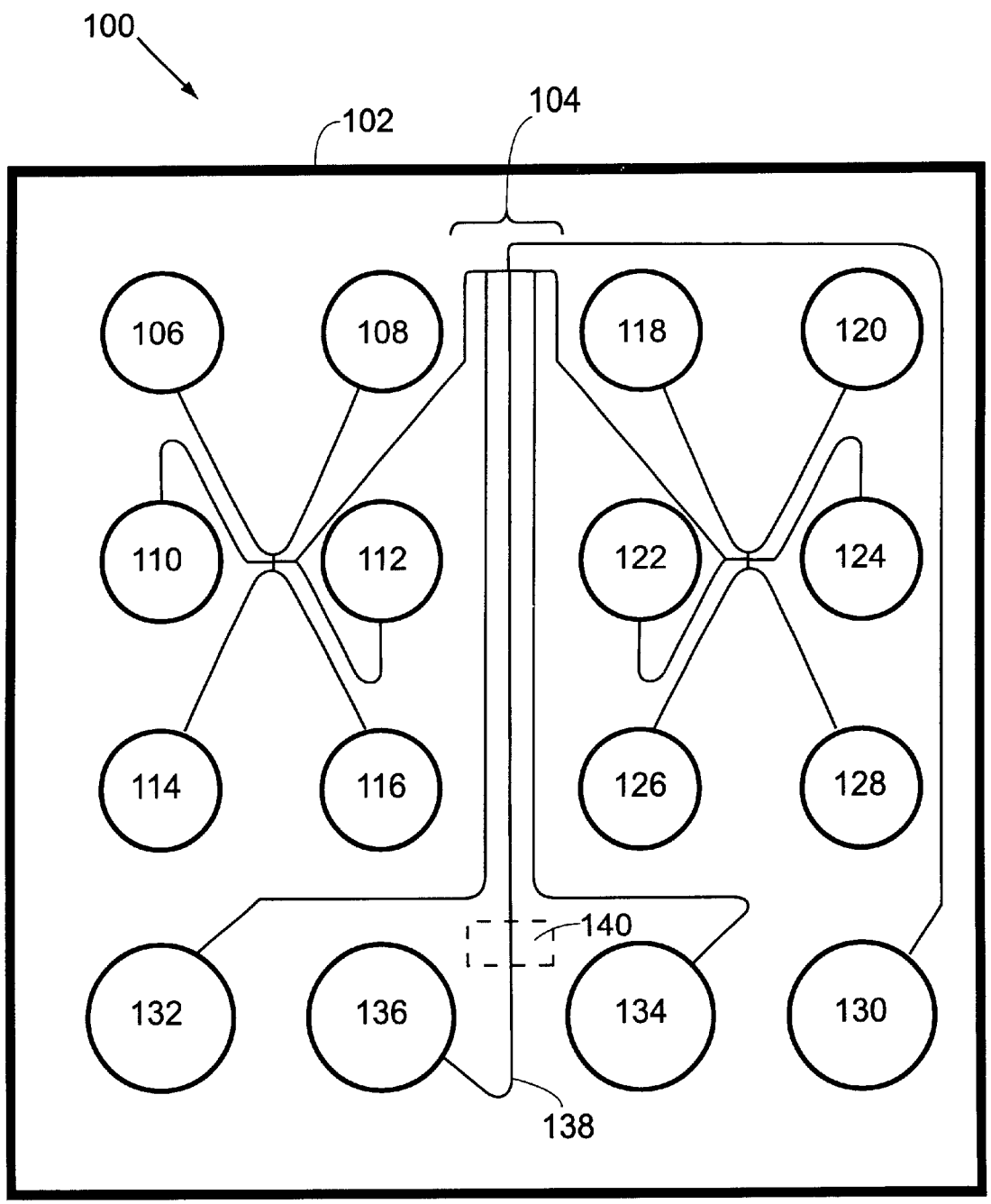
FIG. 1 depicts an example of a microfluidic assay device according to the present invention.

FIG. 1 depicts an example of a microfluidic assay device according to the present invention. As shown, the device 100 includes a body structure 102 which has an integrated channel network 104 disposed therein. The body structure 102 includes a plurality of reservoirs 106–128, disposed therein, for holding reagents, sample materials, and the like. Also included is buffer reservoir 130, as well as waste reservoirs 132, 134 and 136. The reagents, samples, etc. are transported from their respective reservoirs, either separately or together with other reagents from other reservoirs into and along a main channel 138 toward waste reservoir 136, and past detection zone or window 140. Detection window 140 is typically transparent, and may be comprised of a transparent region of the body structure, or a separate transparent window fabricated into the body structure. Typically, the body structure is itself fabricated from a transparent material, e.g., glass or transparent polymers, thereby obviating the need for a separate transparent region to define the detection window. Microfluidic devices of the sort described above are useful in performing a variety of analyses, such as electrophoretic separation of macromolecules, e.g., nucleic acids, proteins, etc. (see U.S. Pat. No. 5,976,336, filed Apr. 25, 1997, and previously incorporated herein by reference), high throughput screening assays, e.g., in pharmaceutical discovery, and diagnostics, e.g., immunoassays (see, e.g., Published PCT Application WO 98/00231). In general, the above device structures and channel geometries, and an infinite number of other similar device structures and channel geometries can be implemented with various aspects of the present invention.

Figure 2:
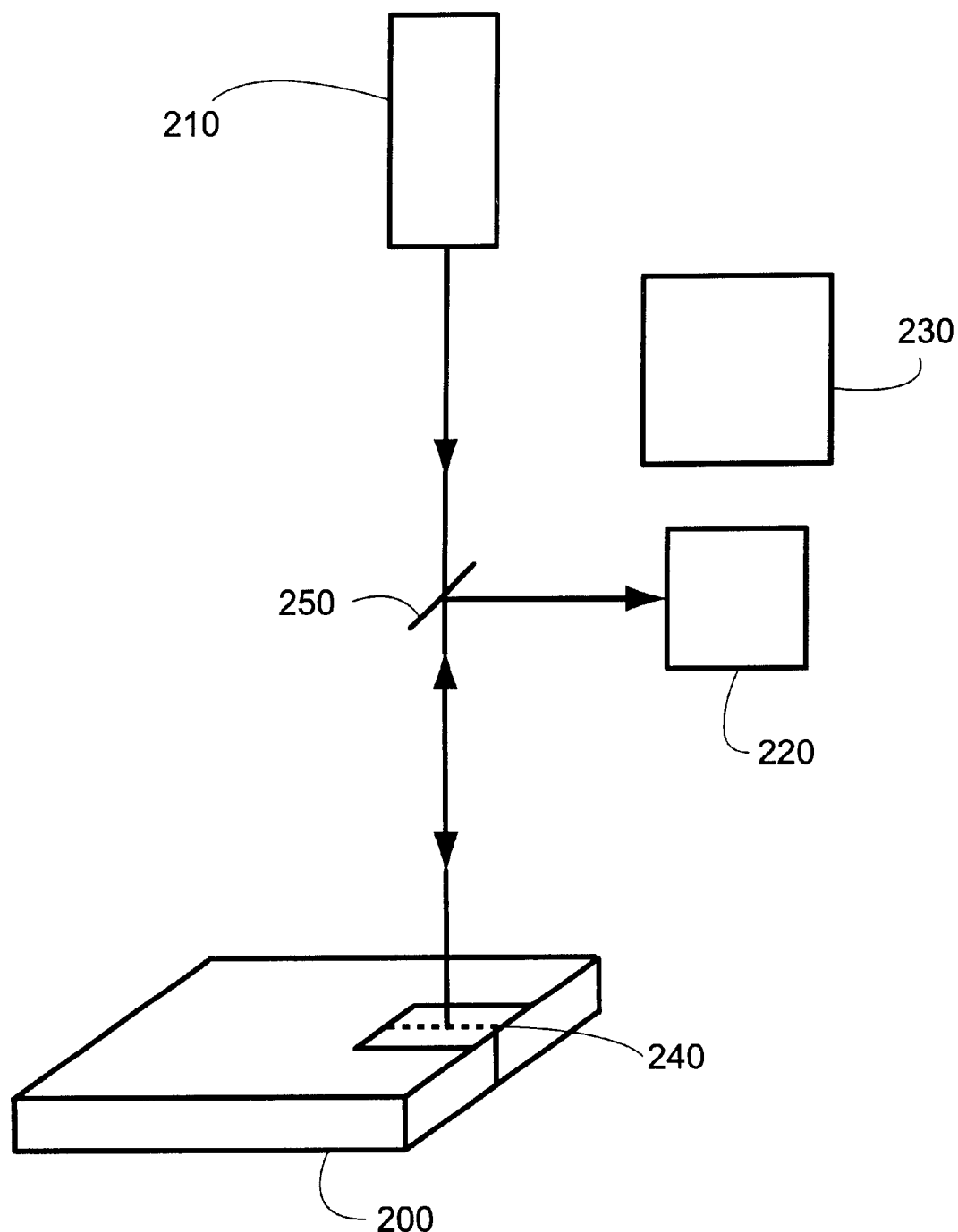
FIG. 2 is a block diagram of an exemplary microfluidic fluorescence detection system 200 according to one embodiment of the present invention.

FIG. 2 is a block diagram of a microfluidic fluorescence detection system 200 according to one embodiment of the present invention. Detection system 200 includes an excitation source 210 configured to illuminate and excite fluorophores in a detection region 240 on chip 200, and a sensor, or detector, 220 for detecting fluorescence emission signals from detection region 240. Fluorescence detector 220 is coupled to a processor 230 which analyzes signals from fluorescence detector 220 to determine information such as fluorescent wavelengths, fluorescence lifetimes, intensities, etc. A beamsplitter element 250, positioned between excitation source 210 and detection region 240, is optionally provided to allow a substantial portion of the excitation signal incident from excitation source 210 to pass through to detection region 240, and to redirect a substantial portion of the radiation incident from detection region 240, including fluorescence emissions, toward fluorescence detector 220. Focussing optics (not shown) focus the incident radiation onto the detection region. In most cases, the microchannel in the detection region defines the focal plane of the focussing optics.

In alternate arrangements, the excitation source can illuminate one or more microchannels in the detection region simultaneously with one or more excitation wavelengths at either a normal or non-normal angle of incidence relative to the plane defined by the detection region on the analysis chip, An example of an illumination and detection system wherein the illumination source illuminates multiple microchannels simultaneously with multiple excitation wavelengths at a non-normal angle of incidence is discussed in U.S. Pat. No. 6,358,387 issued Mar. 19, 2002 entitled "Ultra High Throughput Microfluidic Analytical Systems And Methods," the contents of which are hereby incorporated by reference for all purposes.

Excitation source 210 is a radiation source that outputs radiation in a continuous manner, e.g., a continuous wave laser, or that can be turned on and off very rapidly or which can be modulated rapidly at a rate up to many million times per second, either directly or by using an opto-mechanical device e.g., wave generator, rotating prism or galvanometer mirror. According to preferred aspects, excitation source 210 emits radiation having a wavelength in the range of about 300 nanometers (UV) to about 1000 nanometers (IR). In one embodiment, for example, excitation source 210 is a laser diode that emits visible radiation having a wavelength of approximately 635 nanometers. One suitable laser diode is Hitachi's Laser Diode Model HL6320G.

Excitation source 210 according to alternate embodiments includes other suitable excitation sources such as a HeNe laser or other laser, a flash-lamp, a light emitting diode (LED), or any other controllable radiation source that emits radiation at the desired wavelength(s). Useful lasers suitable for use with the present invention include, but are not limited to, argon ion pumped lasers and mode-locked Ti:sapphire lasers that provide tunable mili-second, nano-second, pico-second or femto-second pulses. Suitable mode-locked Ti:sapphire lasers and ND:YAG lasers are available as models MIRA 900 and INFINITY, respectively from the Laser Products Division of Coherent, Inc. (Palo Alto, Calif.). Other suitable lasers include Nd:YAG lasers such as models ANTARES 76-S, 468-ASE, 7950, 701 and 7049 from the Laser Products Division of Coherent, Inc. (Palo Alto, Calif.). Flash-lamps that generate nanosecond pulses are commercially available. One suitable lamp is available from Photon Technology International (Monmouth Junction, N.J.) and generates 1.6 nanoseconds pulses.

Figure 3:
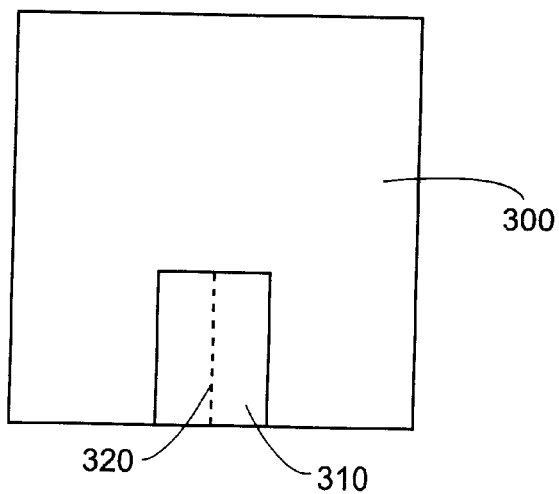
FIG. 3 illustrates a top view of microscale test chip having a slit according to an embodiment of the present invention.

FIG. 3 illustrates a top view of microscale test device 300 according to an embodiment of the present invention. As shown, test device 300 includes a detection area 310 and a slit 320. Device 300 is preferably designed with the same dimensions as an assay chip, e.g., assay device 100, to facilitate placement and orientation in an analytical system employing the assay chip. Detection area 310 is preferably located on test device 300 such that when placed in the analytical system, detection area 310 corresponds to the location of the detection zone or window on a similarly placed assay chip, e.g., detection window 140 of device 100. As shown, detection area 310 is of larger dimension than detection window 140, but it can be of any dimension and geometry sufficient to include all or a portion of the area corresponding to the detection window on an assay chip.

Slit 320 is preferably fabricated on test device 300 in a location corresponding to a microchannel in the detection region on the assay chip. In the case where an assay chip includes a plurality of microchannels in the detection zone, test device 300 can include a corresponding plurality, or subset thereof, of slits. In preferred aspects, each slit 320 has the same or substantially the same dimensions as its corresponding microchannel. Typically, therefore, each slit will have a width of between 0.1 micrometer and about 500 micrometers and preferably between about 1 micrometer and about 100 micrometers. In preferred aspects, test device 300 is made of a glass material, but can be made of any other material, e.g., a silicon substrate processed using standard photolithographic techniques. Detection area 310 in one embodiment includes an opaque material attached to or deposited on device 300, e.g., a layer of metal deposited on device 300 ("metallized" region). For example, according to one specific embodiment, detection area 310 includes a layer of chrome approximately 1000 angstroms thick and slit 320 is between about 10 and about 12 microns wide. Slit(s) 320 can be either fabricated during or after processing of the opaque material. For example, according to one embodiment, a layer of chrome is deposited on the substrate using any of a variety of well known techniques. Thereafter, photoresist is deposited, patterned and etched to define the slit(s) and opaque area at the same time.

Figure 4A:
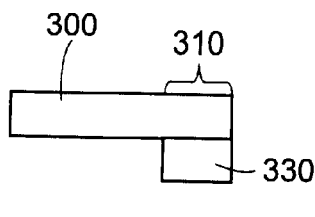
FIGS. 4*a* and 4*b* illustrate side views of the test chip of FIG. 3 coupled to a fluorescent material positioned proximal the slit according to embodiments of the present invention.

FIG. 4a illustrates a side view of test device 300 coupled to a fluorescent material 330 positioned proximal slit 320 according to an embodiment of the present invention. Fluorescent material 330, in this embodiment, positioned outside the body structure of device 300 on the side opposite the illumination source so that the radiation from the illumination source passes through slit 320 and irradiates material 330. Because slit 320 is designed to correspond to a microchannel on an assay chip, slit 320 also determines the focal plane of the illumination from source 210 when positioned appropriately in the analytical system. By positioning the fluorescent material 330 outside the body structure of device 300 as shown, the illumination focussed onto the plane defined by the slit 320 will be "dispersed" when it irradiates fluorescent material 330 in that the intensity of radiation per unit area at the focal plane (e.g., defined by the position of the corresponding microchannel) will be greater than the intensity per unit area at the fluorescent material. Because of the reduced radiation intensity at fluorescent material 330, the resulting fluorescence signal from the fluorescent material 330 will be reduced proportionately. Additionally, the fluorescent material will be less susceptible to photobleaching as photobleaching is a function of the amount of irradiation per unit area.

Figure 4B:
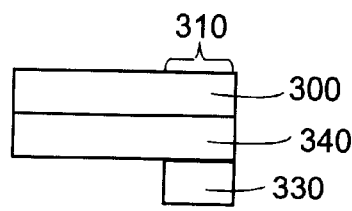

FIG. 4b illustrates a side view of test device 300 coupled to a fluorescent material 330 positioned proximal slit 320 according to another embodiment of the present invention. In this embodiment, a spacer 340 is provided between fluorescent material 330 and device 300. The use of spacer 340 provides a greater distance between the focal plane of the illumination and fluorescent material 330, and therefore a reduced intensity of the radiation irradiating fluorescent material 330. This embodiment is useful when the selected fluorescent material 330 is particularly susceptible to photobleaching and/or would emit too strong of a fluorescence emission signal when positioned proximal device 300 as shown in FIG. 4a, for example. In one embodiment, the width of spacer 340 is on the order of between about 100 micrometers and about 10 millimeters, and preferably between about 0.1 millimeter and about 1 millimeter. By altering the width (dimension separating device 300 from fluorescent material 330) of spacer 340 accordingly, the intensity per unit area of radiation impinging on fluorescent material 330, and therefore also the strength of the resulting fluorescence emissions signal, can be controlled. Although as shown, spacer 340 has the same linear dimensions (e.g., area) as device 300, it will be apparent that spacer 340 can be of any size and geometry sufficient to separate fluorescent material 330 from device 300 by the desired distance.

According to one specific embodiment, test device 300 is made of Schott B270 glass with a thickness of approximately 0.9 millimeter, spacer 340 is made of Schott B270 glass with a thickness of approximately 0.9 millimeter, and fluorescent material 330 includes Ruby having a thickness of approximately 0.12 millimeter.

Figure 5:
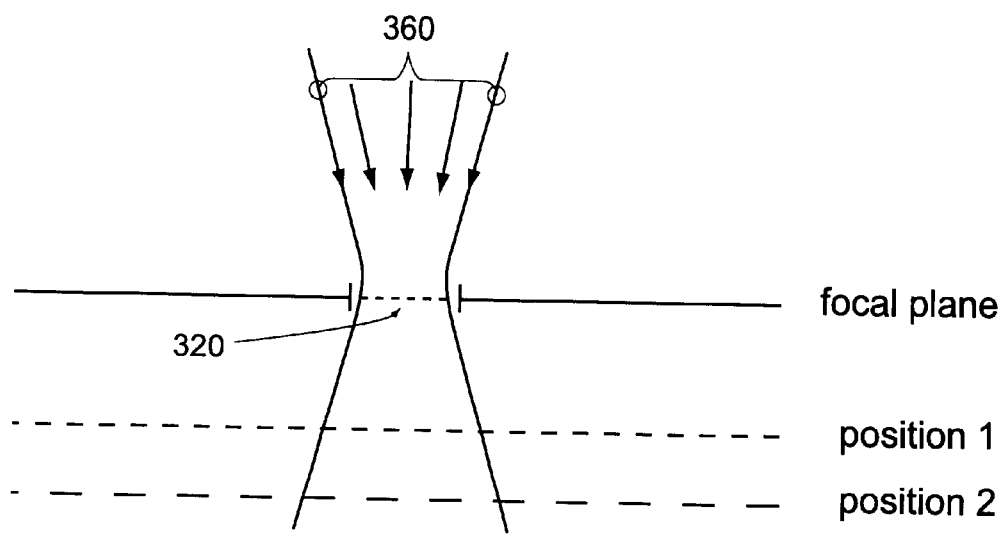
FIG. 5 illustrates a cross section of a focussed light beam impinging on the fluorescent material through the slit according to an embodiment of the present invention.

FIG. 5 illustrates a cross section of a focussed light beam 360 impinging on the fluorescent material 330 through slit 320 according to an embodiment of the present invention. As shown, slit 320 defines the focal plane of the focussed radiation, position 1 represents the position of fluorescent material 330 without the use of spacer 340, and position 2 represents the position of fluorescent material 330 with the use of spacer 340. As can be seen, the focussed radiation beam is dispersed at position 1 relative to the focal plane such that the intensity per unit area at position 1 is reduced relative to the intensity per unit area at the focal plane. Similarly, the intensity per unit area at position 2 is reduced relative to the intensity per unit area at position 1.

Spacer 340 is preferably made of any material that allows fluorescent emissions and excitation signals to pass relatively unhindered, and which also do not themselves fluoresce at the given excitation wavelength. Such materials include glass and quartz. Quartz is preferred for UV applications as quartz does not fluoresce in the UV range.

Although any material that fluoresces can be used as fluorescent material 330, selection of the appropriate fluorescing material will be determined by the specific application and the specific excitation wavelengths used in the analytic system. For example, in one embodiment, fluorescent material 330 includes a sliver of ruby positioned proximal slit 320. Ruby is preferred for wavelengths in the range of about 600 nanometers to about 700 nanometers (red). Also, because ruby provides a strong fluorescent emissions signal and photobleaches readily, a glass spacer is preferably used to increase the dispersion of the excitation signal.

Other useful fluorescent materials include aluminum garnet (primarily for green wavelengths), Labspere SFS 200 (for UV and blue), which is a crystalline structure produced by Labspere, Inc., P.O. Box 70, Shaker Street, North Sutton, N.H. 03260, and any number of inorganic crystals known to fluoresce at various wavelengths. For the Labspere SFS 200, use of a spacer is preferred for UV wavelengths, but is not generally necessary for the blue wavelengths.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A device for use in testing microfluidic fluorescence detection systems having a light source and a detector for detecting fluorescent emissions, the device comprising:
    a test substrate having a mircroslit through which light from the light source is able to pass; and
    a fluorescent material positioned exterior to the test substrate and proximal to or adjacent the microslit opposite light source, wherein the fluorescent material emits a fluorescent emissions signal when light impinges thereon, wherein when light is focused onto th microslit, at least a portion of the light passes through the microslit so as to excite the fluorescent material.

2. The device of claim 1, wherein the microslit has a width of between about 1 micrometer and about 100 micrometers.

3. The device of claim 1, further comprising a spacer located between the test substrate and the fluorescent material for increasing the dispersion of the light impinging on the fluorescent material.

4. The device of claim 3, wherein the spacer is made of a material selected from the group consisting of quartz and glass.

5. The device of claim 1, wherein the fluorescent material includes a material selected from the group consisting of ruby and aluminum garnet.

6. The device of claim 1, wherein the fluorescent material includes an inorganic crystal.

7. A device for use in testing microfluidic fluorescence detection systems having a light source and a detector for detecting fluorescent emissions, the device comprising:
    a test substrate having a microslit through which light from the light source is able to pass; and
    a fluorescent material positioned exterior the test substrate proximal to or adjacent the microslit and opposite the light source, wherein light focused onto the microslit has a first intensity at the microslit, at least a portion of the light passes through the microslit and is dispersed such that the light has a second intensity at the fluorescent material, wherein the second intensity is lower than the first intensity, and wherein the fluorescent material emits a fluorescent emissions signal proportional to the intensity of light impinging thereon.

8. The device of claim 7, wherein the microslit has a width of between about 0.1 micrometers and about 500 micrometers.

9. The device of claim 7, further comprising a spacer located between the fluorescent material and the substrate.

10. The device of claim 9, wherein the spacer is made of a material selected from the group consisting of quartz and glass.

11. The device of claim 7, wherein the fluorescent material includes a material selected from the group consisting of ruby and aluminum garnet.

12. The device of claim 7, wherein the fluorescent material includes an inorganic crystal.

13. A method of testing a microfluidic fluorescent detection system having an excitation source and a fluorescence detector, the method comprising the steps of:

providing a test substrate having a microslit through which light from the excitation source is able to pass, and a fluorescent material positioned external the test substrate and proximal to or adjacent the microslit opposite the light source;

focusing light from the excitation source onto the microslit, wherein at least a portion of the light focussed on the mircroslit passes through the microslit so as to excite the fluorescent material; and detecting fluorescent emissions from the excited fluorescent material with the fluorescence detector.

14. The method of claim 13, wherein the focussed light has a lower intensity at the fluorescent material relative to the intensity at the microslit.

15. The method of claim 13, wherein a spacer is located between the fluorescent material and the test substrate.

16. The method of claim 15, wherein the spacer is one of a glass spacer and a quartz spacer.

17. The method of claim 13, wherein the fluorescent material includes a material selected from the group consisting of ruby and, aluminum garnet.

18. The method of claim 13, wherein the fluorescent material includes an inorganic crystal.

19. The method of claim 13, wherein the microslit has a width of between about 1 micrometer and about 100 micrometers.

20. The method of claim 13, wherein the light emitted by the excitation source has a wavelength in the range of between about 300 nanometers and about 700 nanometers.

* * * * *

UNITED STATES PATENT AND TRADEMARK OFFICE
CERTIFICATE OF CORRECTION

PATENT NO.   : 6,635,487 B1
DATED        : October 21, 2003
INVENTOR(S)  : Lee et al.

It is certified that error appears in the above-identified patent and that said Letters Patent is hereby corrected as shown below:

Column 8,
Line 19, please delete "mircroslit" and insert -- microslit --.
Line 25, please delete "th" and insert -- the --.
Line 34, after "spacer" please insert -- material --.

Column 10,
Line 8, after "and" please delete ",".

Signed and Sealed this

Second Day of March, 2004

JON W. DUDAS
*Acting Director of the United States Patent and Trademark Office*